(12) United States Patent
Fabry et al.

(10) Patent No.: US 8,216,972 B1
(45) Date of Patent: *Jul. 10, 2012

(54) ACID COMBINATION ONE STEP REACTION PROCESS FOR AGRICULTURAL USE PRODUCTS AND ASSOCIATED METHODS

(75) Inventors: Carl J. Fabry, Orlando, FL (US); Vaughn Astley, Lakeland, FL (US)

(73) Assignee: Plant Food Systems, Inc., Zellwood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/094,932

(22) Filed: Apr. 27, 2011

Related U.S. Application Data

(60) Continuation-in-part of application No. 13/035,779, filed on Feb. 25, 2011, which is a continuation-in-part of application No. 13/019,564, filed on Feb. 2, 2011, now Pat. No. 8,088,191, which is a division of application No. 11/349,064, filed on Feb. 6, 2006, now Pat. No. 7,887,616.

(60) Provisional application No. 61/308,569, filed on Feb. 26, 2010, provisional application No. 60/650,378, filed on Feb. 4, 2005.

(51) Int. Cl.
*C05D 1/00* (2006.01)
*C01B 25/163* (2006.01)
(52) U.S. Cl. .............. 504/101; 71/34; 71/41; 71/48; 423/307
(58) Field of Classification Search .............. 71/32, 41, 71/48; 423/307; 424/601; 504/101
See application file for complete search history.

(56) References Cited

U.S. PATENT DOCUMENTS

| | | | |
|---|---|---|---|
| 3,171,733 A | 3/1965 | Hignett et al. | |
| 3,464,808 A | 9/1969 | Kearns | |
| 3,788,817 A * | 1/1974 | Kolbe et al. | 422/198 |
| 3,950,495 A | 4/1976 | Ries | |
| 3,985,538 A | 10/1976 | Hicks et al. | |
| 4,601,891 A | 7/1986 | McGill et al. | |
| 4,637,921 A | 1/1987 | Sansing et al. | |
| 4,724,132 A * | 2/1988 | Fabry | 423/395 |
| 5,736,164 A | 4/1998 | Taylor | |
| 5,800,837 A | 9/1998 | Taylor | |
| 5,925,383 A | 7/1999 | Taylor | |
| 5,997,910 A | 12/1999 | Taylor | |
| 6,338,860 B1 | 1/2002 | Taylor | |
| 6,509,041 B2 | 1/2003 | Taylor | |
| 7,708,799 B2 * | 5/2010 | Grech et al. | 71/29 |
| 2002/0039970 A1 * | 4/2002 | Roberts et al. | 504/206 |
| 2003/0029211 A1 * | 2/2003 | Sheppardson et al. | 71/33 |
| 2006/0159772 A1 | 7/2006 | Garavaglia | |

FOREIGN PATENT DOCUMENTS

WO WO 2005110091 A1 * 11/2005

* cited by examiner

*Primary Examiner* — Wayne Langel
*Assistant Examiner* — Syed Iqbal
(74) *Attorney, Agent, or Firm* — Ralph D. Chabot (57) ABSTRACT

A process for the manufacture of an aqueous composition that is a combination of a fungicide and fertilizer comprising the following steps:
(1) dissolving phosphorous acid in phosphoric acid to form a solution of an acid mixture;
(2) reacting the acid mixture of step (1) with an aqueous hydroxide solution creating an exothermic reaction under pressure; and,
(3) cooling the reaction product to between about 35° C. to about 65° C.
The reaction product prepared according to the above process can also be used as a bactericide.

26 Claims, 1 Drawing Sheet

ACID COMBINATION ONE STEP REACTION PROCESS FOR AGRICULTURAL USE PRODUCTS AND ASSOCIATED METHODS

FIELD OF THE INVENTION

This invention is directed to a process for the manufacture of potassium polyphosphate potassium polyphosphite polymeric compounds, useful for agricultural purposes, as a fungicide, bactericide and a fertilizer.

BACKGROUND OF THE INVENTION

Phosphorus (P) is one of the major elements required by all living species to grow and develop. When the element phosphorus is oxidized to the fullest extent possible, its acid is termed phosphoric acid, [$H_3PO_4$ or $PO(OH)_3$], and the salts of phosphoric acid are termed phosphates, e.g. $K_2HPO_4$. With phosphorus in a slightly less oxidized form, the phosphorus in the acid form is termed phosphorous acid, [$H_3PO_3$, or $HPO(OH)_2$], and the salts of phosphorous acid are termed phosphites, e.g. $K_2HPO_3$. Phosphites are marketed either as an agricultural fungicide, bactericide or without research data as a superior source of plant phosphorus (P) nutrition.

Current commercial methods for making salt compositions from phosphoric acid and phosphorous acid (Phosphorus (P) acids), for foliar application to plants, are carried out by a batch process by separately manufacturing each potassium phosphorus salt. This is accomplished by reacting each P acid with an aqueous base metal hydroxide solution, e.g., potassium hydroxide, sodium hydroxide, ammonium hydroxide, or various combinations thereof, potassium carbonate, or other base metal solutions, into a mixing tank equipped with an agitator and a means of cooling.

As a first step or stage and by an individual process for each P acid, a base potassium solution may be combined with a mineral P acid. As an example a significant quantity of water is added to a typical 1,000 gallon open batch tank. Then 50 pound bags of dry mono potassium phosphate (MKP), which is not completely soluble, are slowly and partially dissolved by continuous agitation and kept agitated while dry bagged potassium hydroxide (KOH) is added. This is a slow, labor intensive, and not a very productive process which only generates a reaction temperature under about 40° C., and is actually only a blend process because MKP is already mostly reacted to a near neutral pH and not very much KOH needs to be added in order to achieve a balanced analysis and pH.

Then as a second step or stage, by an individual process, a base potassium solution may be combined, also separately, with a second P mineral acid. As an example water is added to a typical 1,000 gallon agitated batch tank and then alternately 50 pound bags of phosphorous acid and KOH are combined slowly in order to keep the reaction temperature as low as possible in order to prevent a "run away" reaction and the generation of phosphine gas. The process is very labor intensive, slow and unproductive and is capable of low analysis only.

Thirdly, an additional required step remains wherein these two individually produced potassium salts of each phosphoric and phosphorous acid must be pumped into an agitated batch tank and cold blended to produce a final useful, mixed solution. This is a complicated labor intensive, time consuming, inefficient process which requires additional equipment and storage tanks, and offers more opportunities for error in producing the final product.

In other processes, involving the use of phosphoric acid or by dissolving or wetting of potassium phosphates, such as mono or di-potassium phosphates are subject to a number of problems. The reason that the use of such mono and di-phosphates is desirable in these time proven processes is that most of the exothermic reaction has been completed, thus lending these processes to a safer and simpler but more costly process.

Less common and more dangerous is separately reacting by batch process, phosphoric acid and phosphorous acid with potassium hydroxide or carbonate directly in order to by a third step produce the desired blend mixtures of phosphates and phosphites.

The reactions can be violent and, on a large scale, even with good agitation and cooling, the reaction can "runaway" and has even resulted in fatalities and injuries. During the early stages of this process with either Phosphoric or phosphorous acid, even if the reaction does not "runaway", localized excessive heat release occurs, at under 200° F. (94° C.), and in the case of the phosphorous acid, it is well known in the art that hazardous, toxic phosphine (hydrogen phosphide) gases physically characterized by garlic like malodorous fumes which have decomposed, from the reaction, and are emitted from the batch type reactor which can create a hazard if not properly absorbed and disposed of. In addition, oxygen can very readily be absorbed into phosphorous acid, with the counterproductive decomposition as a result of the oxidation of the phosphorous acid and resultant formation of orthophosphoric acid.

In addition to being more labor intensive, other problems incur in these batch processes due to the necessarily slow addition of materials, in order to prevent "runaway" reactions and the decomposition of phosphorous acid. More problematic is that there is insufficient heat generated with either acid, in the initial part of the reaction with the metal hydroxide solution, thus, preventing the formation of the polymers of phosphorous acid, or of phosphoric acid by heat of reaction. As a consequence, previous processes provide no polymeric conversion of orthophosphorous acid to polyphosphite, or orthophosphoric acid to polyphosphate, because of the imbalance of reactants and/or the insufficient temperature required for the conversion.

Another potential problem which occurs in a batch process is satisfactorily achieving the final pH because extreme caution must be observed in the final stages of the reaction because of the real potential of overshooting the final pH by over addition of either the acid or the base. Precautions must be taken in measuring the ingredients precisely. Careful monitoring is time consuming and lack of attention could lead to an explosion due to a "runaway" chemical reaction. Further, the batch process is known to be more labor intensive and with higher production costs.

U.S. Pat. Nos. 5,736,164; 5,800,837; 5,997,910; 5,925,383; 6,338,860 and 6,509,041 in general describe the blending of individually prepared solutions of potassium orthophosphate and potassium orthophosphite, utilizing only mostly reacted MKP and KOH, by a "batch" process as described above. The processes disclosed are generally labor intensive because dry bagged reactants are carefully, individually added to the batch processes where it is important to keep any heat of reaction as low as possible; because, as in the case of blending phosphorous acid with a base reactant, extreme caution must be exercised in order to prevent "runaway" reactions and to keep the temperature low enough so that poisonous phosphine gasses are not emitted. In any case, phosphate or phosphite polymers are not formed because the high temperatures necessary to produce polymeric compounds are not achieved in a batch process.

These patents describe formulating a potassium phosphate solution separately according to the methods herein described, a mono potassium phosphate is dissolved by the addition of water and further neutralized to desired levels generally with potassium hydroxide.

Both the potassium phosphate and phosphite solutions herein described have long been recognized by the Association of American Plant Food Control Officials (AAPFCO) as fertilizer ingredients, being useful for agriculture and their subsequent use in combined fertilizer mixtures. These patents do not disclose bactericidal attributes.

Then finally, the two individually prepared solutions are "cold blended" combining the two solutions in a third step.

Further, each of the processes disclosed by these patents has one or more of the above problems and disadvantages.

Commercial processes are shown for the preparation of ammonium polyphosphate in Hignett et al. U.S. Pat. No. 3,171,733 and Ries U.S. Pat. No. 3,950,495. Hicks et al. U.S. Pat. No. 3,985,538 shows the use of a pipe reactor to prepare ammonium polyphosphate. These processes result in the conversion of some of the normal orthophosphates to polyphosphates. Processes for improving yields are shown in Sansing et al. U.S. Pat. No. 4,637,921, McGill et al. U.S. Pat. No. 4,601,891, Kearns U.S. Pat. No. 3,464,808 and Ries U.S. Pat. No. 3,950,495. Fabry U.S. Pat. No. 4,724,132 shows a continuous process for the manufacture of a metal salt solution useful for fertilization.

There is a need for a novel process, as provided by this invention that does not rely on the use of MKP in order to form compositions that provide useful agricultural products that not only provide potassium orthophosphates and potassium orthophosphites in a single solution but also in a novel way, compositions that also include potassium polyphosphates and potassium polyphosphites, in a more efficient, safer and more cost effective way, in order to provide a single combination product that is both a superior, more effective fungicide and a safe and effective fertilizer, useful for agriculture.

SUMMARY OF THE INVENTION

The present invention is directed toward a continuous process for the manufacture of a single aqueous solution containing polyphosphates and orthophosphate; and, polyphosphites and orthophosphite compositions. The resulting solution made according to our process, hereafter referred to as reaction product, can be categorized either as a fertilizer compound recognized by AAPFCO containing a phosphate and a phosphite, or as a pesticide compound recognized by the United States Environmental Protection Agency (EPA) as a fungicidal compound containing a phosphate and a phosphite, or any other possible combination of the two. The process comprises the following:

providing phosphorous acid, providing phosphoric acid and providing a base solution selected from either: a) a hydroxide group selected from the group consisting of: aqueous potassium hydroxide, aqueous ammonium hydroxide, aqueous sodium hydroxide, magnesium hydroxide, copper hydroxide, zinc hydroxide, manganese hydroxide or calcium hydroxide or a combination thereof, b) gaseous ammonia, liquid ammonia, or in combination with an hydroxide, or, c) potassium carbonate or in combination with an hydroxide; where the ratio of monovalent cations to phosphorus in mole ratios is between about 1:1 to about 2:1;

providing a continuous reactor for receiving input flow of said phosphorous acid, phosphoric acid and said base solution;

pumping said phosphorous acid, phosphoric acid, in proportion about 50-90 parts phosphoric acid and 10-50 parts phosphorous acid and said base solution while maintaining the ratio of (potassium+ammonium+sodium) to phosphorus in a mole ratio ranging from about 1:1 to about 2:1 so the combined solution flows into said continuous reactor; the combining of said DPA solution and said aqueous hydroxide creating an exothermic reaction under pressure greater than atmospheric and resulting in a reaction product comprising phosphates, polyphosphates, phosphites, polyphosphites and phosphate phosphite copolymers; and, thereafter, cooling said reaction product to below about 35° C. to about 65° C.

Combining phosphorous acid, phosphoric acid and base solution results in an exothermic reaction and this occurs under a pressure greater than atmospheric due to the reaction occurring in a downstream line as opposed to an open-air tank.

Following the exothermic reaction, rapidly cooling the reaction product to reduce the hydrolysis reaction or other degradation of the polyphosphates and polyphosphites formed occurs. Preservation of the polyphosphates and polyphosphites is critical because these compounds act respectively as a fertilizer and bactericide/fungicide when an effective amount of the reaction product is first diluted and then applied to plants.

In a preferred embodiment, the phosphorous acid and phosphoric acid are combined, the combination being defined as a dual phosphorus acid (DPA) solution. Premixing a DPA solution allows for more precise control of the reaction process and reduces the complexity of monitoring the process as only two flow rates have to be monitored rather than three.

Thus, a preferred process for the manufacture of a single aqueous solution containing polyphosphates and orthophosphate; and, polyphosphites and orthophosphite compositions comprises the steps of:

(1) blending a Dual Phosphorus Acid (DPA) solution by either: a) dissolving solid, dry phosphorous acid directly into liquid phosphoric acid; or, b) combining a concentrated solution of phosphorous acid with liquid phosphoric acid;

(2) reacting the DPA solution of step (1) with a base selected from the group consisting of: aqueous potassium hydroxide, aqueous ammonium hydroxide, aqueous sodium hydroxide, magnesium hydroxide, copper hydroxide, zinc hydroxide, manganese hydroxide or calcium hydroxide or a combination thereof while maintaining the ratio of potassium/ammonium/sodium, (monovalent cations), to phosphorus in mole ratios ranging from about 1:1 to about 2:1; and, (3) cooling the reaction product rapidly to below about 35° C. to about 65° C.

In a preferred embodiment, the DPA solution is reacted with potassium hydroxide at a proportion of about 3 parts DPA solution to 4 parts potassium hydroxide. For this process when a DPA is reacted with potassium hydroxide base, the reaction product comprises potassium phosphates, potassium polyphosphates, potassium phosphites, and potassium polyphosphites and potassium phosphate phosphite co-polymers.

As stated earlier, an exothermic reaction between the DPA solution and base occurs that raises the temperature of the mixture to about 50° to about 260° C., preferably about 100° to about 200° C. It is therefore necessary that the DPA solution and base have sufficient concentration in order for the appropriate exothermic reaction to occur. In other words, extremely dilute combination of DPA and base will not generate the desired exothermic reaction and further, the presence of excess water will result in undesired breakdown of the phosphate phosphite co-polymers which are essential for the plant protection offered by this manufacturing process.

In the preferred process described earlier, for step (1), alternative a) is preferred since dissolving dry phosphorous acid directly into liquid phosphoric acid minimizes or eliminates wasteful "added free water", which would hinder the polymerizing reaction. Thus, a concentrated solution is formed having greater reactivity to form phosphorus acid polymers and phosphoric acid polymers. Alternative b) due to more water being present, results in a somewhat weaker solution of both acids.

The phosphoric acid used can be in any commercial or practical concentration, usually from 75% to a 115% $H_3PO_4$ concentration. A concentration over 96% is considered to be super phosphoric acid; however, the preferred concentration is from 85% to 105% for practical commercial acid purchase availability, handling and storage advantage. The DPA solution can be in the range of 1-99 parts phosphoric acid to 99-1 parts phosphorous acid, preferably, about 90-50 parts phosphoric acid to 10-50 parts phosphorous acid.

The reaction product prepared according to the above process is also part of this invention which results in a pesticide composition or a fertilizer composition or any pesticide/fertilizer combination thereof.

DEFINITIONS

In the context of this disclosure, a number of terms are utilized.

The term "about" means within 20%, preferably within 10%, and more preferably within 5% of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "potassium polyphosphate(s)" means polymeric potassium phosphate polymers and includes oligomers, for example, dimers, trimers and the like.

The term "potassium polyphosphite(s)" means polymeric potassium phosphite polymers and includes oligomers, for example, dimers, trimers and the like.

The term "potassium phosphate-phosphite copolymer(s)" means copolymers of potassium phosphates and potassium phosphites.

The term "aqueous potassium polyphosphite solution" means an aqueous mixture formed by the process of this invention wherein aqueous phosphorous acid is reacted with potassium hydroxide and comprises and potassium ortho and polyphosphites, mono-potassium phosphite, and or di-potassium phosphite and forms a pesticidal, bactericidal and/or nutrient solution.

The term "DPA solution" (Dual Phosphorus Acid) means a mixture of phosphorous acid dissolved in phosphoric acid; or, a solution of phosphorous acid blended with phosphoric acid.

The term "reaction product" means an aqueous mixture formed by the process of this invention when a DPA solution and either: a) a hydroxide selected from the group consisting of: potassium hydroxide, ammonium hydroxide, sodium hydroxide, magnesium hydroxide, copper hydroxide, zinc hydroxide, manganese hydroxide or calcium hydroxide or combination thereof; b) liquid ammonia; or, c) gaseous ammonia, are reacted in sufficient concentrations to form stable solutions containing phosphates, polyphosphates, phosphites, polyphosphites and phosphate/phosphite copolymers.

The terms "rapidly cooling" or "cooling the reaction product rapidly" means using any conventional process known to one having ordinary skill in the art to reduce the temperature of the reaction product so that the polyphosphates and polyphosphites present in the reaction product are substantially preserved and hydrolysis or other degradation occurring is de minimus.

The novel process of this invention provides a number of advantages over methods taught in the art. A fungicidal, bactericidal and fertilizer composition is prepared having polymeric components that have a higher analysis with long term storage stability. The reaction product can remain, as a clear solution in storage for extended periods of time without precipitating or "salting out". The reaction product can remain in a clear solution longer than conventionally produced orthophosphorus products.

The polymerized products of this invention can be readily blended with other components, particularly sequestering inorganic metal compounds such as copper, iron, manganese and zinc to form higher analysis, stable compositions that reduce and in many cases eliminate fungal and bacterial activity on a wide variety of plants and crops.

The reaction product can be used as a fertilizer to plants and crops since it comprises a polyphosphate which is well known to be beneficial to plants. Further, there is significantly less foliage burn caused when the products of this invention are applied directly to plants, because of the polymers present in the reaction product of the invention. The polyphosphate and polyphosphite compounds of this invention are also capable of forming soluble complexes with metal impurities by a sequestration process; also, the compositions have activity as a pesticide.

An important aspect of the novel process, which has not been previously recognized, is that the DPA solution can be formed by dissolving orthophosphorous acid directly in orthophosphoric or super polyphosphoric acid without addition of water thereby providing a high concentration of highly reactive acid which is capable of producing polymeric compounds as part of the reaction product of our invention. Less water is present in the novel process thereby concentrating the acid favorably for the formation of polymeric compounds.

Thus, polymer formation is facilitated and increased by the exothermic reaction between the DPA solution and base occurring in a confined space and the increased temperature and pressure greater than atmospheric occurring from the exothermic reaction causes an additional release of water to provide a high concentration reaction product containing phosphate and phosphite polymers, along with residual orthophosphate and orthophosphite compounds. Degradation by hydrolysis of the polyphosphites and related polymers is significantly reduced.

With the use of a continuous reactor, the risk of a "runaway" reaction is eliminated. The unwanted formation of phosphine gas that often occurs in a batch reaction is eliminated by the complete, instantaneous reaction, and rapid cooling process to below critical phosphine formation temperature levels. Only evaporative steam from the heat of reaction, and the dehydration of the phosphate and phosphite moieties in this novel process, is harmlessly discharged to the environment.

Another aspect of this invention is a continuous process for the manufacture of an ortho- and polyphosphite solution which are not only fungicidal and/or nutritional compositions but bactericidal as well, in any combination, that has both pesticidal and/or fertilizer properties. The reaction product can be continuously manufactured wherein phosphorous acid is dissolved in water to formulate a phosphorous acid solution containing between 50%-80% phosphorous acid, which is then reacted with an aqueous base hydroxide solution of sufficient concentration to form aqueous potassium, ammonium, or sodium polyphosphites.

The reaction product has both pesticidal, bactericidal and fertilizer utility.

The DPA solution can have high acid concentrations since super phosphoric acid can be used. The DPA is useful as an intermediate not only in the novel process but also in the formation of other fungicidal and fertilizer products.

Other objects and advantages of the invention will become apparent to those skilled in the art upon reference to the detailed description that hereinafter follows.

DETAILED DESCRIPTION OF THE INVENTION

Figure 1:
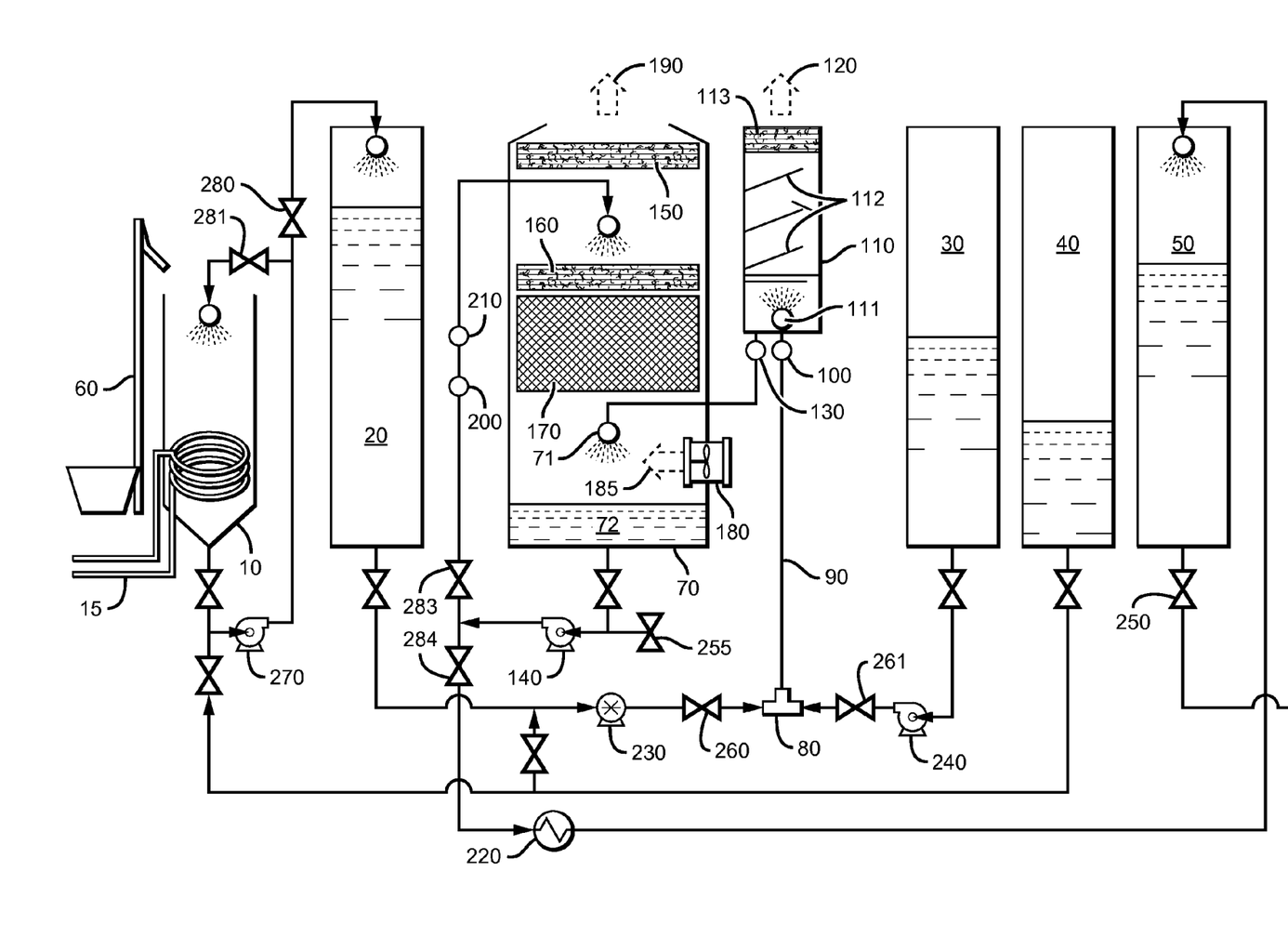
FIG. 1 shows a flow diagram of the process for making the fungicide and fertilizer composition of this invention.

Following in general the flow diagram of FIG. 1, the novel process of this invention is illustrated using phosphoric acid, phosphorous acid and potassium hydroxide for forming the reaction product. First, a measured amount of phosphoric acid is pumped from tank 40 via centrifugal pump 270 though valve 281 either by weight, metering or by visual reference into blend tank 10.

A dry phosphorous acid product from storage is transported, lifted and a measured amount is placed via an elevator 60 likewise into blend tank 10 for dissolving. Other means, either mechanical or labor intensive can be used to put the dry phosphorous acid into blend tank 10. As an option, a pre-dissolved aqueous solution of phosphorous acid can also be used in the place of dry phosphorous acid.

Pump 270 is used to re-circulate the phosphoric acid in blend tank 10 through valve 281 in order to agitate the phosphoric/phosphorous acid combination in order to facilitate the dissolution process while the dry phosphorous is being added to the phosphoric acid. Any acceptable form of agitation can be utilized, including paddle agitation. Upon completion of the dissolution process, the resulting DPA solution can be pumped via pump 270 through valve 280 into storage tank 20 or the DPA solution can be recycled or agitated by pump 270 into blend tank 10 by changing the flow positions of valves 281 and 280.

The phosphoric acid used can be in any commercial or practical concentration, usually from 75% to a 115% $H_3PO_4$ concentration. A concentration over 96% is considered to be super phosphoric acid; however, the preferred concentration is from 85% to 105% for practical commercial acid purchase availability, handling and storage advantage. The DPA solution can be in the range of 1-99 parts phosphoric acid to 99-1 parts phosphorous acid, preferably, about 90-50 parts phosphoric acid to 10-50 parts phosphorous acid.

KOH (potassium hydroxide) solution is stored in tank 30 and is pumped via a constant speed and flow rate pump 240 into reactor tee 80 through a backflow prevention check valve 261.

The DPA solution is pumped from storage tank 20 via a variable speed pump 230 through a backflow prevention check valve 260 into the reactor tee 80. The reaction of the DPA solution and base in or downstream of reactor tee 80, under pressure greater than atmospheric, is virtually instantaneous, and the reaction is further facilitated and evenly completed as the reactants flow through the downstream line 90 having an inline static mixer. From this point forward, downstream line 90 may be interchangeably referred to as in-line static mixer 90. An exothermic reaction between the DPA solution and base occurs that raises the temperature of the mixture to about 50° to about 260° C., preferably about 100° to about 200° C. By this continuous process, the reaction time and travel through the static mixer can be very swift depending on the production rate, usually measured in several seconds.

The ratio of the DPA solution to KOH is maintained at various mole ratios, preferably up to about 2:1 and more preferably from about 1:1 to about 2:1, by controlling and adjusting the flow rate of the acid pump 230. The proper ratio of acid to base is thereby maintained and governed by proper adjustment of the variable speed pump 230, based on the constant monitoring of both the pH and the specific gravity of the reactants as the appropriate adjustments are then made to pump 230 as the DPA solution is pumped into reactor tee 80, while pump 240 stably pumps the KOH solution at a constant rate into reactor 80. The reaction product is being formed between reactor tee 80 and through in-line static mixer 90 where the reaction of KOH and the DPA solution is completed.

The KOH solution is an aqueous solution and can be purchased and received as such (or formed from dry flake KOH) that contains about 25-95 wt %, preferably about 40-60 wt % and more preferably about 50 wt % KOH.

Reactor tee 80 is a typical conventional reactor custom manufactured and assembled on site in a "tee" configuration to the proper specifications. Any conventional continuous reactor known to those skilled in the art can be used but reactor tees connected with a tubular pipe section having a static inline mixer are preferred. Useful reactor tees and their tubular components can vary in diameter from about 1-12 inches or more in diameter, depending on the desired production flow rate, residence time desired for the reaction for optimum polymer formation, and by other factors. The diameter and length of the continuous reactor, typically tubular, are critical factors; however, the ratio of length to diameter is most useful. The ratio of length to diameter should be between about 20 and 5. A more preferred ratio is between 15 and 6.

Typically, a 2 inch diameter tubular reactor is used wherein the KOH solution is pumped into the reactor at a rate of between about 20 and 40 gpm with the preferred rate being about 29 gpm. The DPA solution is pumped into the reactor at a rate between about 15 and 40 gpm with the preferred rate being about 21 gpm.

The temperature control is achieved primarily by simultaneous and proportional flow reduction or increase of the DPA solution relative to the flow of the KOH. The "high" reaction temperature is measured in the reactor in the pipe leading from it via a thermal gauge 100. The process temperature is between about 65° C. and about 260° C. Either or both of the reactants may be preheated by various means, an outside heat source or including heat transfer from the reaction or the finished product cooling, in order to reach temperatures higher than about 175° C., while maintaining sufficient product cooling.

The actual residence time in reactor tee 80, through static mixer 90, the piping and prior to entering steam disengagement unit 110, is very rapid because of high flow rates and the instantaneous removal of water by the heat of reaction, resulting in elevated pressures and the generation of steam. The residence time is calculated from the volume of reactor tee 80, through static mixer 90, the piping and prior to entering steam disengagement unit 110, divided by the volume pumped in per minute. The residence time calculated in this manner is preferred to be between about 0.01 and 1.5 minutes. A more preferred residence time is between about 0.02 and 1.0 minute; however longer residence times could produce even higher polymer content.

Reactor tee 80 is used in combination with a tubular pipe reactor 90 which includes a static in-line mixer which facilitates complete reaction; although, a sufficient reaction is possible without such a peripheral inline mixing device in conjunction with the reactor tee. A typical in-line mixer useful in the process of this invention is disclosed in Horner U.S. Pat. No. 4,093,188. This particular in-line mixer has stationary baffles providing a turbulent, non-parallel spiraling path to effect a more thorough and efficient blending of fluids. Other conventional static in-line mixers can be used in the process as disclosed in Katzen U.S. Pat. No. 3,190,618, Chisholm U.S. Pat. No. 3,652,061 and Sluijters Re. 28,072. The length and configuration of the in-line mixer is such that the reaction is substantially completed before cooling of the reaction product. If an in-line mixer were not used in the process, the tubular reactor would have to be lengthened to insure a substantially complete reaction.

Thermal gauge 100 measures the temperature of the reaction product as it leaves static in-line mixer 90. It is essential that the temperature of the reaction product be maintained in about the 50° to about 200° C. range in order to produce the highest polymer content possible while preventing hydrolysis of polymers formed in the reaction product by residual water that is present.

The reaction product is then passed into the steam disengagement unit 110 wherein the temperature of the reaction product is reduced to between about 25° to 75° C. Typically, if the reaction temperature is about 200° C., the temperature should be rapidly reduced to about 65° C. and then further reduced to about the 30° to about the 40° C. range.

It is essential to maintain the evaporative cooling tank 70 pool temperature below about 70° C. and product temperature to storage below about 35° C. in order to minimize hydrolysis of polyphosphates or polyphosphites back to their ortho-forms.

Variations in the rapid reduction of the temperature will be required depending on the initial temperature of the reactants, the concentration of the reactants and the like. In this unit, water in the form of steam 120 is instantaneously released from the reaction product and vented to the atmosphere and accounts in part for the necessary first step in the rapid temperature drop of the reaction product in order to preserve polymer content. Rapid cooling is important in order to obtain and preserve high yield of polyphosphates and polyphosphites in order to reduce the hydrolysis reaction or other degradation of the polymers formed.

Steam disengagement unit 110 comprises a pressure reduction nozzle 111 which reduces the temperature of the reaction product by diffusing the reactant pressure, evacuating steam by a series of baffles 112 which further provide a reduction of temperature and a demister pad 113 that prevents loss of reaction product which condenses on the pad and flows back into unit 110. Steam 120 condenses to water vapor as it passes out of the unit to the atmosphere. The reaction product then passes through to evaporative cooling tank 70, through temperature gauge 130, and out through a spray nozzle 71 which further disengages any residual steam and the reactant is then further cooled by air by an axial flow evaporative cooling fan 180 to further reduce the temperature of the reaction product to desirable levels. Evaporative cooling is typical to those familiar with the art. Ambient temperature air 185 is injected, blown, and forced through packing element 170 while the hot reactant product is re-circulated by pump 140 through valve 283 through temperature gauge 210 and pH meter 200 exiting onto a fluid diffuser plate 160 and passing through the packing 170 in which the packing comprises shaped pieces of polyvinyl chloride and reactant flowing down through that packing, evaporatively cooling, and on down to the bottom of the evaporative cooling tank 70. As air passes up through the packing 170 while simultaneously the hot reactant is passing down over packing 170, steam and heat 190 is released which passes through diffuser plate 160 and up and out through demister pad 150 which serves to prevent any blown reactant passing on through harmlessly to the atmosphere and to the environment.

Pump 140 not only pumps hot reactant over the packing for cooling, but also simultaneously bypasses and directs a certain portion of that production flow of now cooled and finished reactant, now product, through a metering finished product storage control valve 284 to final product storage tank 50. Production balance, between the reactants going into the process, evaporation losses together with maintaining a constant fluid level in the process control tank and cooling tower result in a continuous equilibrium between production and storage.

The reactor level control is maintained and cooling as measured by temperature gauge 200 and a pH of about 4.5 to about 8.50 measured by pH meter 200 is achieved by carefully monitoring and controlling the production flow rate through the reactor tee by maintaining a steady reactant product heel level 72 in evaporative cooling tank 70.

If additional cooling is required in order to maintain and preserve maximum polymer content, a conventional heat exchanger 220 such as, a plate and frame or tube and shell, can be added prior to delivery in to product storage tank 50. The resulting product is then sent to product storage tank 50 through product control valve 284, for ultimate shipping and distribution via product storage tank valve 250.

In reference FIG. 1, the size of tanks 10 and 20 containing acid or potassium hydroxide tank 30 is immaterial as long as they contain sufficient material to produce a continuous reaction and the desired amount of product. A separate tank that contains other minor ingredients, such as secondary nutrients and micronutrients, can be used in the process but these minor ingredients are not utilized to such an extent to significantly change the ratio of the DPA solution to KOH solution in the reaction. The tubular reactor 90 and reactor tee 80 only function using liquid feeds. Hence, the DPA solution and the KOH solution must be liquids.

An unexpected and important advantage of the process for forming a reaction product is that polyphosphate and polyphosphite can be prepared simultaneously. The process of this invention produces high yields of polyphosphate if a mixture of phosphorous acid and phosphoric acid is used instead of phosphorous acid alone. The advantages of having a mixture of both acids include less handling, lower manufacturing, storage, and blending costs; however, the most important advantage of our invention is that the reaction product possesses bactericidal qualities. The reaction product now allows simultaneous application of a fungicide, a bactericide, and a fertilizer, the application of which synergistically enhances crop growth, more so than if each product was separately applied. The presence of nutrients makes possible quick, vigorous growth of the crop enabling the crop to more effectively compete with pests which are simultaneously controlled by the DPA's fungicide and bactericide combination, thereby increasing the effective utilization of the fertilizer. Applying nutrients in combination with a fungicide and a bactericide will enhance the effectiveness of the fungicide and bactericide on its pest on target. Also, the presence of both acids in the process provides for the formation of copolymers, that is, polymers containing both phosphite and phosphate groups. Such copolymers are new materials and not simply a mixture of polyphosphite and polyphosphate. However, chemical analysis of such polymers is difficult.

The novelty of the reaction product is that it provides simultaneous fungicidal and bactericidal activity to plants and fertilizer to plants. In particular, potassium phosphite provides fungicidal activity, with the potassium polyphosphite being a superior fungicide and a bactericide, and when both hydrolyze and oxidize after application and exposure to the elements, they form phosphate ions that fertilize the plant.

When plants are treated with phosphites they will absorb and store phosphites. However, plants cannot use phosphites as a phosphorus nutrient source, but require that phosphates be applied in order to meet plant phosphorus needs. The absorption and storage of phosphite triggers a mechanism in the plant wherein the plant will not absorb phosphate which is the nutrient the plant requires for normal healthy growth and the plant will exhibit the characteristics of phosphate starvation. Therefore, the phosphate compounds in the reaction product are an absolute necessity to provide orthophosphorus to the plants that is absorbed by the plants and provides the fertilizer component that is required for plant growth and development. Both the polyphosphates and polyphosphites of this invention are xylem and phloem mobile and are rapidly absorbed and translocated within the plant at the point of leaf contact within 24 hours. The reaction mixture has shown to be highly effective and curative by quickly reversing the fatal effects of Citrus Greening Disease, and by restoring vigorous normal growth, enhancing fruit set, size, color, and increasing yields with higher pounds solids.

Fertilizers formulated from the DPA solution have a threefold advantage, nutritional, fungicidal and bactericidal because Phosphate and Phosphite identification, signaling and movement is identical in plants through Phosphate transporters. Plants cannot utilize Phosphites as a nutritional sole source of Phosphorus based on research from the early 1950s. Thus, if only Phosphites have been applied, increasing their levels in the plant, and Phosphorus levels were previously low or deficient, the plant is not able to differentiate the difference and interprets through signaling transporters that Phosphorus levels are adequate to sustain plant growth and health, while interfering with many of the Phosphorus deficiency responses in plants and yeast (*Saccharomyces cerevisiae*). This phenomenon is known as "Phosphate Starvation." Various plant genes that express Phosphorus sufficiency are thereby suppressed when Phosphites alone are applied to Phosphorus deficient plants, causing the plant to respond in a normal, adequate Phosphorus healthy way, when in fact the opposite is true, making it much more susceptible to nutritional and disease disorders and ultimately yield losses and perhaps mortality. The reaction product of this invention solves this plant signaling problem by simultaneously providing both Phosphate and Phosphite in a homogeneous polymeric bond that signals both Phosphorus nutritional sufficiency within the plant, and in the case of Citrus Greening Disease, Phosphite bacteriological for disease control as well.

The reaction product can be blended with components, such as, urea to provide a nitrogen component and also with effective amounts of secondary nutrients such as, calcium, magnesium, sulfur, and micronutrients such as, boron, copper, iron, molybdenum, manganese and zinc to form a high quality fungicide, bactericide and a fertilizer. Also, the reaction product can be cold blended with a variety of agriculture products for application by growers or can be sold as an intermediate to growers to blend with other agricultural products. Stable clear and sprayable compositions are formed.

After manufacture the reaction product can be kept in storage tanks, as a clear, stable solution for a long period of time. Typically it can have a Nitrogen, Phosphorus, Potassium (NPK) ratio, expressed as weight percentage, of, 0-23-25 to 0-26-26 and sold as such or diluted with other nutrients or water for specific uses. The reaction product can be sprayed directly onto crops, or diluted by other nutrient additives, in an effective amount depending on the crop and the desired effect that is wanted to reduce disease damage and or fertilize the crop.

Potassium phosphite provides fungicidal activity but the potassium polyphosphite is a superior fungicide, and bactericide, and when the phosphite becomes hydrolyzed and oxidized after application phosphate ions are formed which provide fertilizer to the plant. All the products of this invention are recognized and can be cold blended with most other fertilizer nutrient materials, particularly most inorganic metal compounds.

Typically, analytical laboratories determine total $P_2O_5$ content by oxidation and hydrolysis of all the phosphorus containing species into their orthophosphate form, and also determine an ortho-$P_2O_5$ expressed as, orthophosphate, without any oxidation or hydrolysis being carried out. Both determinations are carried out using the approved industry standard methods which utilize the phospho-molybdate colorimetic orthophosphate analytical procedure. All other phosphate species which do not analyze as "orthophosphate", are non ortho-species, and are relegated as "polyphosphates and reported as such. This procedure is easier to understand for "ammonium polyphosphate" determinations, because there is no other possible source of "non ortho-" except polymerized phosphate species; however, in the case of simple phosphorous acid compounds, all the phosphorus therein also analyzes as a "non ortho-" species and is therefore also assigned its value totally, for the entire sample as a "polyphosphate, confusingly as well.

In the present invention, this problem is solved by knowing the amount, or the ratio that was used in each formulation, of the orthophosphorous acid, and the orthophosphoric acid used in the formulation of the DPA solution. When the total phosphate content, together with the orthophosphate content (because of the presence of orthophosphoric acid) is reported, the difference is assigned as total polyphosphate content, i.e. non-ortho-. The known value or contribution of the phosphorous acid present, to the total polyphosphate value, can then be subtracted and the balance then reliably to be stated to be the formed polyphosphate and/or polyphosphite, as illustrated in table 1-1 below.

However, the most effective and practical way to determine if polymers of phosphoric or phosphorous acid have been produced, is by comparing the physical difference and the physical properties of ortho-solutions as compared to those differences and properties of this invention. The following are all physical characteristics and attributes of ammoniated polyphosphates which compare favorably with those potassium salt based polyphosphates and polyphosphites of this invention, as compared to orthophosphates and orthophosphites, which include: significantly higher analysis, longevity in storage without precipitation or "salting out", remaining a crystal clear solution, blending capability with inorganic metal nutrient compounds with little or no precipitation, and significantly better crop response.

The following examples illustrate the invention. All parts and percentages are on a weight basis unless otherwise indicated.

EXAMPLES

Example 1

Referring to FIG. 1, first a measured amount of 85% phosphoric acid was pumped from tank 40 via pump 270 into blend tank 10. Next, solid dry 99% phosphorous acid was transported to blend tank 10 and lifted into blend tank 10 via elevator 60 and blended, agitated and mixed with pump 270 with the 85% phosphoric acid and dissolved therein. A continuous feed ratio of 1:3 by weight of phosphorous acid to phosphoric acid was maintained during the process. The resulting DPA solution was then preheated by an external source of steam through heating coil 15, from ambient temperature to about 82° C. in order to obtain a higher heat of reaction temperature in reactor tee 80. To begin the test, a 3,000 gallon per hour production rate was established which would require a 29 GPM per minute flow rate of KOH and 21 GPM flow rate of phosphoric acid when production was fully up to specification. A "resident" 300 gallon starter heel of finished product was left in the reactor vessel from the previous run in order to prime the evaporative cooling system with similar product so that cooling of the first, hot reacted product entering the reactor vessel would be instantaneous. The process can also be started up using a water heel for instantaneous evaporative cooling, but is not as desirable as starting up on finished goods because this water dilution of the initially produced product needs to then be worked off during the entire run and can result in a lower polymer concentration. The variable speed KOH pump 240 was started at the full anticipated flow rate of 29 GPM. A constant speed pump can also be used with a manifold by pass system with two distribution valves on the discharge side of the pump. One valve can direct the appropriate amount of product on through to the reactor, with a second control valve which can bypass excess pumped material back to the KOH product storage tank. As soon as KOH flow was established into the evaporative cooling tank 70 through reactor tee 80, the variable speed acid pump 230 was then immediately started pumping the DPA solution from tank 20 into reactor tee 80, and likewise through the system into evaporative cooling tank 70, at an acid pumping rate of approximately 16 GPM, or 75% of the anticipated full production capacity to ultimately be achieved, in order to begin the initial reaction. Almost immediately a pulsing jet like roaring like sound was heard from evaporative cooling tank 70, as the reactants impinged, in a violent reaction in the tee 80. Temperature gauge 100 immediately began to rapidly climb from ambient temperature to about 100° C. Also immediately a pulsing, tall steam plume began evolving out of the top of evaporative cooling tank 70 in uneven bursts, indicating an unbalanced reaction in the tee 80. After evaluating the startup process and observing their were no anomalies the DPA solution pumping RPM and pumping rate were increased slowly to approximately 21 GPM where the reaction began to smooth out, and the pulsing reaction stopped, the steam plume changed to a smooth, steady stream as the reaction came into perfect balance as the reactor began to run more quietly and efficiently. As the reaction temperature began to rise to near maximum capacity, the temperature peaked at about 172° C. In order to establish the maximum reaction run temperature, because daily atmospheric differences can affect both the reaction and the evaporative cooling temperature in this process, the full and optimum reaction temperature was verified by adding slightly more acid to the reaction, where the temperature began to drop off slightly from the maximum just achieved, verifying the maximum reaction temperature of about 172° C. for the balance of this run. At this point pH and specific gravity, product monitoring began as previously specified and the run temperature was adjusted periodically to maintain maximum operating efficiency. The rpm and subsequent output of the DPA solution pump was very slightly altered during the run in order to maintain a stable production pH of about 8.00. The run was continuous for 3 hours producing approximately 9,000 gallons of finished product.

No free water was added continuously during the run to the reactor to control final product specific gravity, which was allowed to climb to its maximum level and remained constant at 1.57. The reaction temperature did not fluctuate and remained about a constant 172° C. Periodic 1,000 ml sub-samples were taken, and combined in a common container and a single representative sample drawn of the entire days run and submitted to a commercial laboratory familiar with testing ammoniated phosphorus compounds for polymerization. Total $P_2O_5$ and Ortho-$P_2O_5$ determinations were made in order to determine the "non ortho-" or polymerized species using approved industry standard methods which utilize the phospho-molybdate colorimetic analytical procedure, with the highest polymerization results listed below as sample #1, in Table 1-1.

Example 2

Example 2 was procedurally similar to Example 1, including a run temperature of about 170° C. in tee 80, except that the specific gravity was lowered and closely monitored and maintained at 1.48 by continuously adding free water to evaporative cooling tank 70 via injection port valve 255 on the suction side of cooling, recirculation and product deliver pump 140. Sampling procedure and handling were also similar to Example 1, and the results are listed below as Sample #2, in table 1-1, which showed less polymerization because of the added free water and lower specific gravity in the reaction process than the results from Example 1.

Example 3

Example 3 was procedurally similar to Example 2. The run temperature was about 174° C. in tee 80. The specific gravity was lowered still more and closely monitored and maintained at 1.47 by continuously adding free water to evaporative cooling tank 70 via injection port valve 255 on the suction side of cooling, recirculation and product deliver pump 140. Sampling procedure and handling were also similar to example 2, and the results are listed below as Sample #3, in Table 1-1, which showed even less polymerization because of the added free water and lower specific gravity in the reaction process than the results from example 2.

Example 4

Example 4 was procedurally similar to Example 3. The run temperature was about 170° C. in tee 80. The specific gravity was lowered still more and closely monitored and maintained at 1.45 by continuously adding additional free water to evaporative cooling tank 70 via injection port valve 255 on the suction side of cooling, recirculation and product deliver pump 140. Sampling procedure and handling were also similar to Example 3, and the results are listed below as Sample #4, in Table 1-1, which showed less polymerization because of the additional, added free water and lower specific gravity in the reaction process than the results from Example 3.

TABLE 1-1

| # | pH | SG | Total P₂O₅ | Ortho P₂O₅ | Total Poly Phosphate | Non Ortho From H₃PO₃ | Net Poly Phosphate Poly Phosphite | Total Percent Polyphosphate PolyPhosphite | Free H₂0 |
|---|---|---|---|---|---|---|---|---|---|
| 1 | 8.30 | 1.57 | 23.9% | 6.7% | 17.2% | 5.4% | 11.8% | 49.3% | None |
| 2 | 8.20 | 1.48 | 23.4% | 15.0% | 8.4% | 5.3% | 3.1% | 13.3% | 1X |
| 3 | 8.00 | 1.47 | 22.8% | 14.4% | 8.4% | 5.2% | 3.2% | 14.2% | 2X |
| 4 | 8.00 | 1.45 | 23.2% | 15.8% | 7.4% | 5.3% | 2.1% | 9.3% | 3X |

Example 5

Example 5 was conducted in order to determine and show the effectiveness of applying fertilizer mixtures formulated with the reaction product as opposed to nutrient solutions formulated only with phosphite. A two fold comparative test was conducted to determine if phosphate starvation could be prevented, and the effectiveness of the reaction product formulated from DPA solutions to demonstrate effectiveness in order to prevent, suppress or control Huanglongbing, Citrus Greening Disease, a bacterial disease of citrus which is currently threatening citrus crops world wide with extinction. The disease is transmitted by psyllids which are small piercing sucking insects. Huanglongbing symptoms include small yellow leaves with a mottled or blotchy appearance and yellow veins exhibiting mineral deficiencies such as Manganese and Zinc, twig and branch dieback, sparse, small fruit that is abnormal in appearance and fails to color properly, thus the name greening, with aborted seeds and poor juice quality and finally rapid degeneration into a non-productive state and mortality.

In test treatment #1, four reaction products and micronutrient treatments were made at six week intervals to citrus trees exhibiting moderate to severe Greening symptoms. In treatment #2, four Phosphite alone treatments, with micronutrients was applied. In treatment #1 the Greening symptoms reversed within six months and visually the tree returned to a normal healthy state and productive state. In treatment #2 the Greening symptoms have gotten worse with tree removal the inevitable solution. Treatment #1 shows an ideal level of 0.18% in the leaf tissue Phosphorus levels, while the Phosphorus level in treatment #2, 0.12 percent, is severely deficient. The results are shown in table 2-1.

TABLE 2-1

| | Percent | | | | | | | PPM | | | | |
|---|---|---|---|---|---|---|---|---|---|---|---|---|
| # | N | P | K | Mg | Ca | Na | S | B | Zn | Mn | Fe | Cu |
| 1 | 3.05 | 0.18 | 1.58 | 0.34 | 5.20 | 0.02 | 0.37 | 80 | 45 | 50 | 90 | 16 |
| 2 | 2.83 | 0.12 | 1.23 | 0.31 | 3.95 | 0.06 | 0.37 | 60 | 29 | 26 | 45 | 7 |

Example 6

Example 6 was conducted in order to show the systemic properties and the bacterial disease control effectiveness of the potassium polyphosphite solution produced as a result of this invention as compared to the previously determined orthophosphite crop non-responses.

Phosphites in general are known to move systemically upward and downward throughout the entire plants vascular system, translocating to the new growth, via both the xylem and the phloem. Orthophosphites, are only registered or recommended for foliar application as "nutritionals", or as a fungicide for certain fungal control. The nutritional efficacy of phosphites, as a source of phosphate, has never been demonstrated and their use as a "nutritional" is simply to skirt pesticide regulatory laws. In cases where soil application was attempted, there was no beneficial crop response and even severe crop damage has occurred. Spray tank mixes with Copper are also avoided because of the occurrence of severe crop damage.

Xanthomonas citri subsp. Citri., bacterial citrus canker, is a leaf, fruit, and stem blemishing disease, by the bacterial penetration of the stomatal pores. When weather and high wind-driven rain is not a factor, canker is primarily dispersed, or the plant tissue invaded, as a result of insect damage, mechanical exposure or injury, wounds made by thorns where present, and blowing sand.

The bacterium reproduces in lesions on leaves, stems and fruit, where with free moisture, the bacteria ooze out and spread to new growth and other trees. Initially small lesions occur on leaf surfaces which saturate the intercellular spaces with water, and then destroy epidermal plant cell structure, by secreting cell wall degrading enzymes, toxins and extracellular polysarrharides (EPS). Plants fight off disease pressure through natural, self defense, disease suppression or elimination methods, which occur through rapid cytological action, and by triggering other plant cellular phytoalexin accumulations and metabolic changes and other disease resistance inducers. As a result, tree health is ultimately determined by its cells ability to effectively produce and transport antibacterial disease fighting compounds.

Historically there has been no evidence that orthophosphites have any control over Citrus canker and their use is not labeled or recommended for that purpose. All phosphite based pesticides are registered as a foliar treatment for fungal diseases only, and not for any bacterial diseases. Based on their labeled specifications orthophosphites cannot be tank mixed with copper fungicidal compounds because of phytotoxic injury to plant tissue with that combination.

The test was set up for both foliar and soil application, and tank mixes with copper. Applications of polyphosphite, both with and without added copper were tank mixed, and applied to citrus trees with severe citrus canker symptoms. The purpose was to test for any citrus canker control, phytoxicity to the trees, and for systemic plant self defense responses. It rapidly became evident that the polyphosphite was able to demonstrate that plant self defense mechanisms were activated. Within a week after foliar application and about two weeks after soil application, a yellowing, "walling off halo effect" of each individual new lesion, somewhat like a fire line around a forest fire, was observed. This is characteristic of a systemic plant self defense response where walling off of the surface lesions occurs, stopping the lesions from enlarging and spreading to adjoining leaves. There was no plant phytotoxicity of leaf tissue observed from either singular applications of the polyphosphite or from the tank mix combination with copper. The disease cycle appeared to be stopped, and further colonization, sporulation, reproduction, and dissemination of the bacteria to the entire tree, and adjoining trees seemed to be achieved. The polyphosphite was curative, by acting within the fungal cell walls to visually stop, inhibiting further fungal or bacterial growth, by direct toxicity to plant pathogens. This was the observation because inside the yellow halo effect, where the lesion had been, a dry dead spot appeared in about 30 days and ultimately dried out as a black dead spot of tissue, and dropped out of the leaf, leaving an open "shot hole" in the leaf where the lesion had occurred. The second observation made was that apparently natural, self defense mechanisms, systemic acquired resistance (SAR) and induced resistance (IR) were induced because the disease did not spread further in the plant tissue, from the initial lesions.

The tank mix with copper, as a surface protectant and the polyphosphite as an internal systemic agent, proved to be a good combination, providing control on the surface of the leaf before infection and systemic post control of bacterial sporulation incubation.

The invention as fully described above may embody other specific forms or variations without departing from its spirit or essential characteristics. In that regard, the embodiments described above are to be considered in all respects as illustrative and not restrictive, the scope of the invention being indicated by the claims rather than by the foregoing description and any and all changes that come within the meaning and range of equivalency of the claims are intended to be embraced therein.

We claim:

1. A process for the manufacture of an aqueous fungicide, bactericide and fertilizer solution comprising the following steps:

(1) dissolving phosphorous acid in phosphoric acid to form a solution of an acid mixture;

(2) reacting the acid mixture of step (1) with an aqueous hydroxide solution selected from the group consisting of: potassium hydroxide, ammonium hydroxide sodium hydroxide, magnesium hydroxide, copper hydroxide, zinc hydroxide, manganese hydroxide, calcium hydroxide or a combination thereof; at a temperature of about 65° C. to about 260° C. in a continuous reactor while maintaining the ratio of mono-valent cations potassium/ammonium/sodium to phosphorus in a molar ratio from about 1:1 to about 2:1, and the ratio of di-valent cations magnesium/copper/zinc/manganese/calcium to phosphorus in a molar ratio from about 0.5:1 to about 1:1 thereby forming a reaction product comprising phosphates, polyphosphates, phosphites, polyphosphites and phosphate phosphite copolymers; and, (3) rapidly cooling the reaction product to between about 35° C. to 65° C.

2. The process of claim 1 wherein the acid mixture comprises about 50-90 parts phosphoric acid and 10-50 parts phosphorous acid.

3. The process of claim 1 wherein the continuous reactor is a tubular pipe reactor and the acid mixture is fed into the tubular reactor at a rate of about 15 to 30 gallons per minute simultaneously with the aqueous hydroxide solution which is being fed into the reactor at a rate of about 15-40 gallons per minute and the acid mixture and hydroxide solution are reacted for about 0.01-1.5 minutes.

4. The process of claim 3 wherein the aqueous hydroxide solution comprises about 40-60% by weight potassium hydroxide, ammonium hydroxide, sodium hydroxide or a combination thereof.

5. The process of claim 4 wherein said rapidly cooling comprises passing the reaction product through a steam disengagement unit whereby water present in the reaction product is vaporized thereby rapidly cooling the reaction product and the reaction product is further cooled by spraying the mixture into an air stream and recycling reaction product with reaction product entering cooling area thereby cooling the reaction product to between about 25° C.-75° C.

6. The reaction product made according to claim 1 having a pH of about 4.5 to about 8.50.

7. The reaction product of claim 6, where an effective amount can be diluted with water and used as a bactericide.

8. The reaction product of claim 6, where an effective amount can be diluted with water and used for treating a plant for a microbial infection.

9. The reaction product of claim 6 further comprising agricultural components selected from the group consisting of nitrogen compounds, secondary nutrients, micronutrients and any mixtures thereof.

10. The reaction product of claim 6 further comprising an effective amount of copper where the resulting solution can be foliarly applied for plant fungicidal, bactericidal and/or nutritional benefit without injury to plants.

11. The reaction product of claim 6 where an effective amount can be diluted with water and applied to soil for plant fungicidal, bactericidal, and/or nutritional benefit to plants.

12. A process for the manufacture of a concentrated fungicide and fertilizer solution comprising the following steps:

providing a Dual Phosphorus Acid (DPA) solution comprising about 50-90 parts phosphoric acid and 10-50 parts phosphorous acid;

providing an aqueous hydroxide solution selected from the group consisting of: potassium hydroxide, ammonium hydroxide, sodium hydroxide, or a combination thereof wherein the weight % of said potassium hydroxide, ammonium hydroxide, sodium hydroxide, or a combination thereof is between about 40-60% of said aqueous hydroxide solution;

providing a continuous reactor for receiving input flow of said DPA solution and said aqueous hydroxide solution;

pumping said DPA solution and said aqueous hydroxide solution while maintaining the ratio of (potassium+ammonium+sodium) to phosphorus in a mole ratio ranging from about 1:1 to about 2:1 so the combined solution flows into said continuous reactor; the combining of said DPA solution and said aqueous hydroxide creating an exothermic reaction under pressure greater than atmospheric and resulting in a reaction product comprising phosphates, polyphosphates, phosphites, polyphosphites and phosphate phosphite copolymers; and, thereafter, rapidly cooling said reaction product to below about 35° C. to about 65° C.

13. The DPA solution of claim 12 comprising the dissolving of solid, dry phosphorous acid directly into liquid phosphoric acid.

14. The DPA solution of claim 12 comprising the mixing of liquid phosphorous acid with liquid phosphoric acid.

15. The process of claim 12 wherein the continuous reactor is a tubular pipe reactor.

16. The process of claim 15 wherein the residence time within said tubular pipe reactor is between about 0.01-1.5 minutes.

17. The process of claim 15 wherein rapidly cooling of the reaction product comprises passing the reaction product through a steam disengagement unit whereby water present in the reaction product is vaporized thereby cooling the reaction product and the reaction product is further cooled by spraying the mixture into an air stream and recycling reaction product with reaction product entering cooling area thereby cooling the reaction product to between about 25° C.-75° C.

18. The reaction product made according to claim 12 having a pH of about 4.5 to about 8.50.

19. The composition of claim 18, where an effective amount is diluted with water and used as a bactericide.

20. The composition of claim 18, where an effective amount is diluted with water and used to treat a plant for a microbial infection.

21. The composition of claim 18 further comprising agricultural components selected from the group consisting of nitrogen compounds, secondary nutrients, micronutrients and any mixtures thereof.

22. A process for the manufacture of an aqueous fungicide and fertilizer solution comprising the following steps:
(1) providing a Dual Phosphorus Acid (DPA) solution comprising about 50-90 parts phosphoric acid and 10-50 parts phosphorous acid;
(2) reacting the acid mixture of step (1) with either liquid ammonia or gaseous ammonia in a continuous reactor while maintaining the ratio of ammonia to phosphorus in a molar ratio from about 1:1 to about 2:1 thereby forming a reaction product comprising ammonium phosphates, ammonium polyphosphates, ammonium phosphites, ammonium polyphosphites and ammonium phosphate phosphite copolymers; and,
(3) rapidly cooling the reaction product to between about 35° C. to 65° C.

23. A process for the manufacture of an aqueous fungicide and fertilizer solution comprising the following steps:
providing a phosphoric acid solution;
providing a phosphorous acid solution;
providing an aqueous hydroxide solution selected from the group consisting of: potassium hydroxide, ammonium hydroxide, sodium hydroxide, or a combination thereof wherein the weight % of said potassium hydroxide, ammonium hydroxide, sodium hydroxide, or a combination thereof is between about 40-60% of said aqueous hydroxide solution;
providing a continuous reactor for receiving input flow of said phosphoric acid solution, said phosphorous acid solution and said aqueous hydroxide solution;
simultaneously pumping said phosphoric acid solution, said phosphorous acid solution and said aqueous hydroxide solution into said continuous reactor, where the combined solutions of liquid phosphoric acid and liquid phosphorous acid is between 50-90 parts phosphoric acid and between 10-50 parts phosphorous acid and while maintaining the ratio of potassium/ammonium/sodium (potassium+ammonium+sodium) to phosphorus in a mole ratio ranging from about 1:1 to about 2:1; the combining of said solutions creating an exothermic reaction under pressure greater than atmospheric and resulting in a reaction product comprising phosphates, polyphosphates, phosphites, polyphosphites and phosphate phosphite copolymers; and,
thereafter, rapidly cooling said reaction product to below about 35° C. to about 65° C.

24. The process of claim 23 wherein the continuous reactor is a tubular pipe reactor and the combined solutions of phosphoric acid and phosphorous acid are fed into said tubular reactor at a rate of about 15 to 30 gallons per minute simultaneously with said aqueous hydroxide solution being fed into said tubular reactor at a rate of about 15-40 gallons per minute.

25. The process of claim 24 wherein the residence time within said tubular pipe reactor is between about 0.01-1.5 minutes.

26. The process of claim 25 wherein cooling of the reaction product comprises passing the reaction product through a steam disengagement unit whereby water present in the reaction product is vaporized thereby rapidly cooling the reaction product and the reaction product is further cooled by spraying the mixture into an air stream and recycling reaction product with reaction product entering cooling area thereby cooling the reaction product to between about 25° C.-75° C.

* * * * *